April 14, 1970 SEIZO SUZUKI Plant Pat. 2,968
ROSE PLANT
Filed May 29, 1968
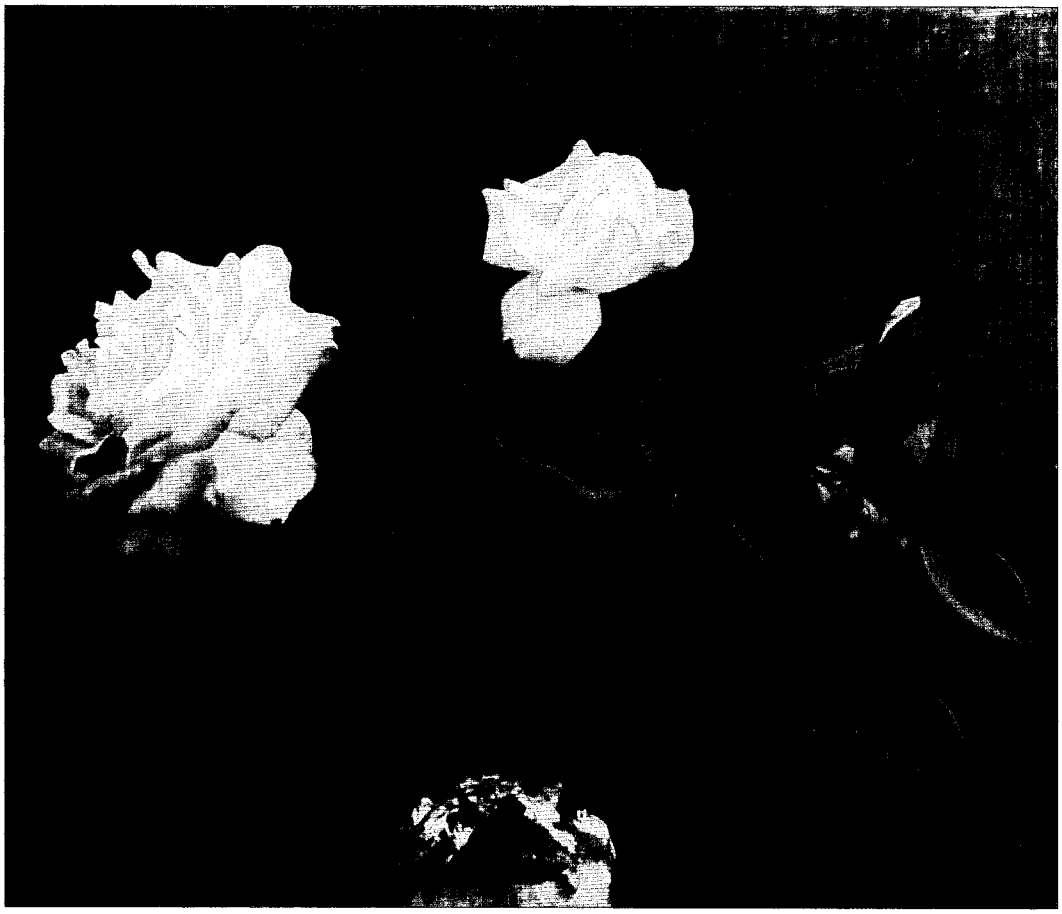

United States Patent Office

Plant Pat. 2,968
Patented Apr. 14, 1970

2,968
ROSE PLANT

Seizo Suzuki, 324 3-chome, Tamagawa-Okusawa-cho, Setagaya-ku, Tokyo, Japan

Filed May 29, 1968, Ser. No. 733,196
Int. Cl. A01h 5/02
U.S. Cl. Plt.—11 1 Claim The invention relates to a new and distinct variety of rose plant of the hybrid tea class originated by me in 1958 as a consequence of a breeding program begun in 1954. The parentage of my new rose plant is as follows:

Rose Gaujard (P.P. 1829) × Crimson Glory (P.P. 105)

The object of the cross was to get the largest bicolor flower of warm red and white which becomes deeper bright red at maturity, with good substance, and also to get a vigorous plant.

These objectives were achieved along with other desirable improvements, as evidenced by the following unique combination of characteristics which are outstanding in the new variety and which distinguish it from its parents as well as from all other varieties of which I am aware. My new variety is primarily characterized by: continuous medium-large blooms of good substance which are bicolor of white and red until the half-open stage and change gradually into wholly bright red as they open in the sun, and by especially disease resistant, strong, vigorous plants with beautiful foliage.

Asexual reproduction of my new variety by grafting and budding, through a series of annual propagations at Owada, Yachiyo, Chiba Prefecture, Japan shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of field and container grown plants under greenhouse and field conditions at Livermore, Orland, San Marten and Santa Rosa, Calif., U.S.A. and Owada, Yachiyo, Chiba Prefecture, Japan.

Vigorous, sturdy, upright plant, moderately branching. 30"–48" in height.

The foliage is abundant, smooth, leathery, semi-glossy to glossy. Leaflets 3–7, average 5, generally ovate with pointed tips and serrated margins, ⅜"–1¾" wide x ¾"–2¾" long. The new leaf is Sage Green (HCC 000861) very lightly overlain with Chysanthemum Crimson (HCC 824/5) on the upper side and Spinach Green (HCC 0960/2) lightly overlain with Chrysanthemum Crimson (HCC 824/5) on the underside. The mature leaf is Sage Green (HCC 000861) on the upper side and Spinach Green (HCC 0960/2) on the underside. The leaf is odd pinnate. The petioles are 1"–1½" colored Chrysanthemum Crimson (HC 824/3. Ribs and veins are conspicuous, on new foliage midrib is Chrysanthemum Crimson (HCC 824/3) on upper surface, lower very faintly tinted with Chrysanthemum Crimson (HCC 824/3). The rachis is Chrysanthemum Crimson (HCC 824/3).

There are thorns and some prickles. The young thorns are Purple Madder (HCC 1028/1) and the mature thorns are straw to tan. They are 1/32–⅜" tall, 1/32–⅛" wide, ⅛"–⅜" long. The amount varies from numerous stiff, bristle-like thorns near base of smaller canes to 7 per 3" stem, 5 nodes from the inflorescence. Slightly hooked.

The flower bud opens slowly, is long and pointed, becoming urceolate. Of medium size, 1⅛"–1⅜" long, 3⅝"–¾" in diameter. When sepals first divide, the bud is Pansy Purple (HCC 928/2), when sepals begin to unfurl, the bud is Pansy Purple (HCC 928/2). The sepals are not appendaged; they curl back as they unfurl and are moderately branched. Outside is Spinach Green (HCC 0960) heavily overlain and streaked with Oxblood Red (HCC 00823); inside, Lavender Green (HCC 000761). The hypantheum is about ½" in diameter x about ⅜" long, smooth outside, hairy inside, funnel form. The peduncle is about 1½", strong, erect to slightly curved. The color is Spinach Green (HCC 0960) heavily overlain and streaked with Oxblood Red (HCC 00823) outside, Lavender Green (HCC 000761) inside.

The flower is of medium-large size, about 1⅝" in depth, about 4½" in diameter; high centered when bloom first opens, flattens somewhat as bloom matures. The petals are imbricated, 30–36 in number, obovate; waxy to silky in appearance, almost leathery. The outer petal is Pod Green (HCC 061/3) at the base becoming white, then becoming Tyrian Purple (HCC 727/1) at the tip. The inner petal is Pod Green (HC 061/3) at the base becoming white, then Phlox Pink (HCC 625/1) at the tip. The reverse on the inner petal is the same as the front; the reverse on the outer petal is the same only with much less white. 1¼"–2" white and 1½"–2⅛" long. The petaloids are 8–12, ¼"–1¼" wide by ⅝"–1½" long. Color similar to petals only streaked with Phlox Pink (HCC 625/1). The stamens are ½" long, whorled in arrangement, plus or minus 145. Filaments 5/16" long, pink in color. Very prominent disc ½" in diameter, 3/16" thick, raised 1/16". Inner stamens turned inward with anthers tucked between disc and styles. Style is pink, about 90 pistils, ¼"–6/16" in the length. Stigmas are creamy yellow. Moderate tea rose fragrance. The ovaries of ordinary character. The fertility is not good on pollination, but after fertilization it has big fruit (half inch) including few seeds. The color of the fruit is light green for the first one month and then changed to reddish-yellow when the fruit is in mature. The seed is always bigger than the seed of ordinary rose plants.

Having thus disclosed my invention, I claim:

1. A new and distinct variety of rose plant of the hybrid tea class substantially as herein shown and described primarily characterized by: continuous medium-large blooms of good substance which are bicolor of white and red until the half-open stage and change gradually into wholly bright red as they open in the sun, and also by the especially disease resistant, strong, vigorous plant with beautiful foliage.

No references cited.

ROBERT E. BAGWILL, Primary Examiner